United States Patent [19]
Theodoridis et al.

[11] Patent Number: 6,080,702
[45] Date of Patent: Jun. 27, 2000

[54] HERBICIDAL HETEROCYCLIC BENZISOXAZOLES AND BENZISOXAZOLIDINONES

[75] Inventors: George Theodoridis, Princeton; Lester L. Maravetz, Westfield; Scott D. Crawford, Bordentown, all of N.J.

[73] Assignee: FMC Corporation, Philadelphia, Pa.

[21] Appl. No.: 09/043,737

[22] PCT Filed: Oct. 2, 1996

[86] PCT No.: PCT/US96/15826

§ 371 Date: Sep. 14, 1998

§ 102(e) Date: Sep. 14, 1998

[87] PCT Pub. No.: WO97/12886

PCT Pub. Date: Apr. 10, 1997

Related U.S. Application Data
[60] Provisional application No. 60/004,874, Oct. 4, 1995.

[51] Int. Cl.[7] .......................... A01N 43/54; A01N 43/66; A01N 43/80; C07D 413/10
[52] U.S. Cl. .......................... 504/215; 504/216; 544/212; 544/309; 544/310; 544/311; 544/312; 548/241
[58] Field of Search ................................. 504/215, 216; 544/212, 309, 310, 311, 312; 548/241

[56] References Cited

U.S. PATENT DOCUMENTS

| | | | |
|---|---|---|---|
| 3,920,442 | 11/1975 | Albert et al. | 71/92 |
| 3,920,653 | 11/1975 | Wenzelburger et al. | 260/256.4 C |
| 4,881,967 | 11/1989 | Semple | 71/92 |
| 5,169,431 | 12/1992 | Enomoto et al. | 71/92 |
| 5,484,763 | 1/1996 | Wepplo | 504/269 |
| 5,521,147 | 5/1996 | Theodoridis | 504/243 |
| 5,578,627 | 11/1996 | Takeda et al. | 514/379 |

FOREIGN PATENT DOCUMENTS

| | | |
|---|---|---|
| 0 255 047 A1 | 2/1988 | European Pat. Off. |
| 0 355 827 A2 | 2/1990 | European Pat. Off. |
| 0 408 382 A2 | 1/1991 | European Pat. Off. |
| 0 420 194 A2 | 4/1991 | European Pat. Off. |
| 0 476 697 A1 | 3/1992 | European Pat. Off. |
| 0 640 600 A1 | 3/1995 | European Pat. Off. |

OTHER PUBLICATIONS
Wrubel, Chem. Abstract 92:181062,1980.

*Primary Examiner*—Mukund J. Shah
*Assistant Examiner*—Deepak R. Rao
*Attorney, Agent, or Firm*—FMC Corporation

[57] ABSTRACT

Disclosed are herbicidal heterocyclic benzisoxazoles and benzisoxazolidinones of formula (I):

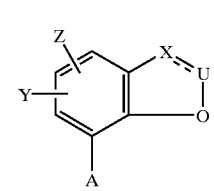

(I)

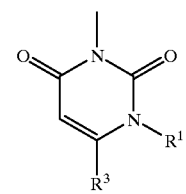

(a)

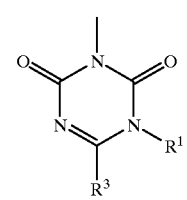

(b)

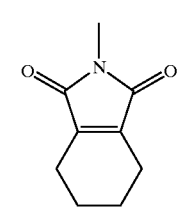

(c)

wherein A is (a), (b) or (c); U is N or NR; X is CO or $CR^2$; and R, $R^1$, $R^2$, $R^3$, Y and Z are as disclosed in the disclosure.

28 Claims, No Drawings

HERBICIDAL HETEROCYCLIC BENZISOXAZOLES AND BENZISOXAZOLIDINONES

This application is a 371 of PCT/US96/15826 filed Oct. 2, 1996 which claims the benefit of Provisional Application No. 60/004,874 filed Oct. 4, 1995.

BACKGROUND OF THE INVENTION

The present invention relates generally to weed control in agriculture, horticulture, and other fields where there is a desire to control unwanted plant growth. Particularly, the present invention relates to certain herbicidal 3-(benzisoxazol-7-yl and 1,2-(2H)-benzisoxazolidin-3-on-7-yl)-heterocycles and certain derivatives and novel intermediates thereof. More particularly, the present invention relates to certain herbicidal (benzisoxazol-7-yl and 1,2-(2H)-benzisoxazolidin-3-on-7-yl)-heterocycles wherein the heterocycle is a 2,4-(1H, 3H)-pyrimidinedione, a 4,5,6,7-tetrahydro-1H-isoindole-1,3-dione, or a 1,2,5,6-tetrahydro-1,3,5-triazine-2,6-dione.

U.S. Pat. No. 5,169,431 discloses herbicidal uracil derivatives of formula:

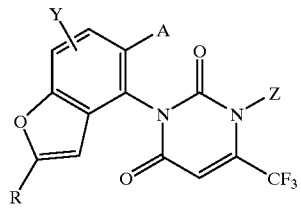

wherein: R=alkyl; A and Y=H or halogen; and Z=methyl or amino.

U.S. Pat. No. 5,521,147 discloses herbicidal compounds of the formula:

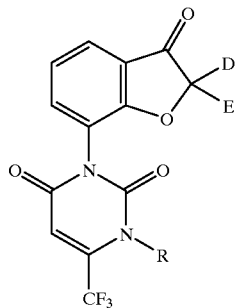

where D and E are independently H or alkyl and R is alkyl or amino.

SUMMARY OF THE INVENTION

It has now been discovered that certain 3-(benzisoxazol-7-yl and (2H)-benzisoxazolidin-3on-7-yl)-heterocycles where the heterocycle is a 2,4-(1H, 3H)pyrimidinedione, a 4,5,6,7-tetrahydro-1H-isoindole-1,3-dione, or a 1,2,5,6-tetrahydro-1,3,5-triazine-2,6-dione have good activity as both pre- and post-emergence herbicides, especially on weeds in crops such as wheat, corn, and soybeans. The compounds are also effective as general dessicants that are useful in total vegetation control. This invention also relates to novel intermediates which are useful for making the herbicidal compounds.

DETAILED DESCRIPTION OF THE INVENTION

The novel compounds of the present invention have the following generic structure:

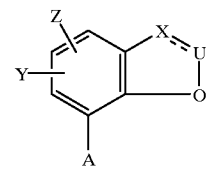

wherein A is

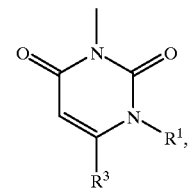

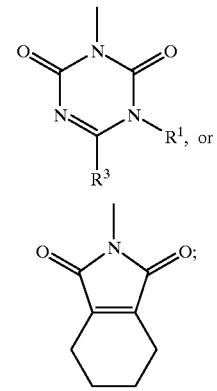

U=(a) N and X is attached to U by a double bond or (b) NR and X is attached to U by a single bond;

R=H, alkyl, alkenyl, alkoxycarbonylalkyl, (alkoxycarbonyl)haloalkyl, benzyl, phenyl, or cyanoalkyl;

X=(a) CO when U is NR or (b) $CR^2$ when U is N;

$R^1$=H, alkyl, haloalkyl, or amino;

$R^2$=halogen, alkyl, alkoxy, cyanoalkoxy, phenyl optionally substituted with one or more halogen or alkyl groups, alkoxycarbonyl, alkoxycarbonylalkoxy, benzyl, benzyloxy, or haloalkyl;

$R^3$=alkyl or haloalkyl;

Y=H, halogen, cyano, or haloalkyl;

Z=H or halogen.

As used in this specification, the terms "alkyl," "alkenyl," "alkynyl," "haloalkyl," and "alkoxy" used alone or as part of a larger moiety, includes straight or branched carbon chains of 1 to 6 carbon atoms. "Halogen" refers to fluorine, bromine or chlorine. "THF" means tetrahydrofuran, "DMF" means N,N-dimethylformamide, and "DBU" means 1,8-diazabicyclo[5.4.0]undec-7-ene.

Preferred compounds of the present invention include those of formulae II and III:

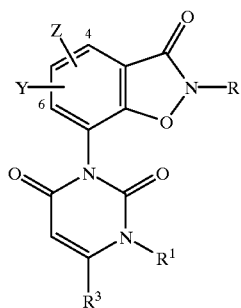

II

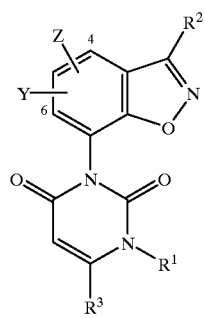

III wherein: R=CH$_3$, CH$_2$CH$_3$, or CH(CH$_3$)$_2$; R$^1$=CH$_3$, CHF$_2$, or NH$_2$; R$^2$=CH$_3$ or phenyl; Y=4-Cl, 4-Br, or 4-CN; Z=6-F, 6-Cl, or 6-H; and R$^3$=CH$_3$ or CF$_3$. Particularly preferred are compounds of formula II or III wherein: R=CH$_3$, CH$_2$CH$_3$, or CH(CH$_3$)$_2$; R$^1$=CH$_3$ or NH$_2$; R$^2$=CH$_3$; Y=4-Cl or 4-Br; Z=6-F or 6-H; and R$^3$=CH$_3$ or CF$_3$.

Certain intermediates of the present invention are novel. These include compounds of formulae IV and V:

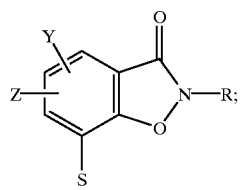

(IV)

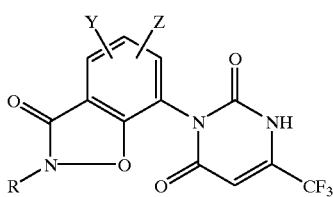

(V)

wherein: R, Y and Z are as defined above for formula I, II, or III, and S=NH$_2$, NHCO$_2$-alkyl, or N=C=O.

Compounds of the present invention represented by formula II may be prepared as shown in Scheme I below. An appropriately substituted chlorophenylcarboxylic acid is nitrated to give nitrobenzoic acid A which may be converted to the benzamide C in two steps via the acid chloride B. C undergoes cyclization with DBU to the corresponding (2-alkyl-7-nitro-substituted)-1,2(2H)-benzisoxazolidin-3-one (D). Reduction of the nitro group of D with iron in acetic acid provides the amino intermediate E, as described below in Example 6. Alternatively, when Y or Z is Br (for the purpose of directing the nitration in step a), catalytic hydrogenation of the nitro group with 10% Pd/C causes concomitant removal of the Br. Halogen substituents may be optionally introduced by reacting E with an N-halo succinimide. Examples 2–5 provide details of these procedures.

The isocyanate group of F is then cyclized with 3-amino-4,4,4-trifluoro-2-butenoate in the presence of an appropriate base in an inert solvent to form the pyrimidinedione ring of G. Examples of appropriate bases include organic bases such as triethylamine, pyridine, and N,N-diethylamine, and inorganic bases such as sodium hydride and potassium carbonate. Examples of inert solvents that may be used include aromatic hydrocarbons such as benzene and toluene, halogenated hydrocarbons such as chloroform and carbon tetrachloride, ethers such as diethyl ether, dioxane and tetrahydrofuran, and DMF and dimethylsulfoxide. The reaction temperature is preferably about 20°–80° C. The pyrimidinedione ring may then be variously substituted by N-alkylation with an R$^1$-halide (step h in Scheme 1) to provide compounds such as II-A, or by N-amination with 1-aminooxysulfonyl-2,4,6-trimethylbenzene in a suitable solvent such as THF in the presence of a suitable base such as K$_2$CO$_3$ to provide compounds such as II-B. Examples 1, 2, and 3 provide details of this procedure.

For obtaining compounds of the present invention where the R$^3$ group of II is CH$_3$ rather than CF$_3$, ethyl 3-amino-4,4,4-trifluorocrotonate in the above reaction is replaced by ethyl 3-aminocrotonate. For obtaining compounds of the present invention where the R$^1$ group of II is CHF$_2$, the corresponding compound having R$^1$=H may be heated in a mixture of DMF and potassium carbonate to about 120° C., followed by bubbling chlorodifluoromethane through the reaction mixture for about one-half hour.

SCHEME 1

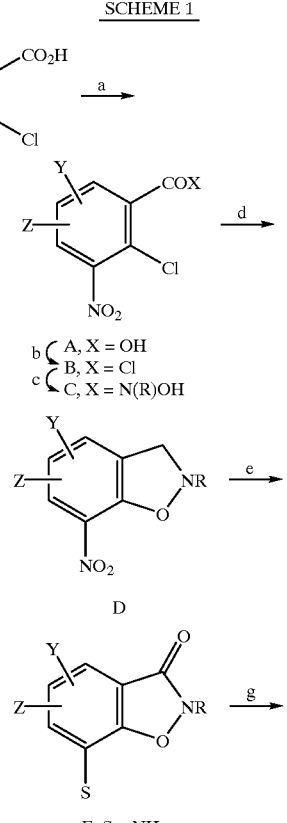

-continued

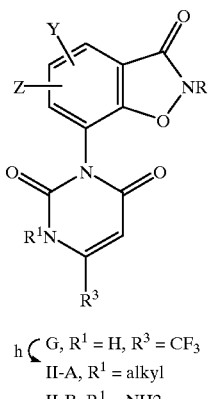

h ( G, R¹ = H, R³ = CF₃
II-A, R¹ = alkyl
II-B, R¹ = NH2 a) HNO₃/H₂SO₄, 30–35° C.; (b) SOCl₂ or oxalyl chloride, warm; (c) NH(R)OH, Et₂O, NaHCO₃, H₂O; (d) DBU, CH₃CN, warm; (e) Fe, HOAc, H₂O, 40–50° C.; (f) ClCO₂CCl₃, toluene, dioxane, warm; (g) CF₃C(NH₂)=CHCO₂CH₂CH₃, NaH, THF, warm; (h) R¹X, K₂CO₃, DMSO, warm; (i) 1-aminooxysulfonyl-2,4,6-trimethylbenzene, K₂CO₃, THF Compounds of the present invention of formula III may be prepared as shown in Scheme 2 below. The choice of starting material depends on whether $R^2$ is phenyl or alkyl. If $R^2$=phenyl, a 2-halo-benzophenone is treated with triethylamine and hydroxylamnihe hydrochloride to form the corresponding benzophenone oxime H-1. If on the other hand $R^2$=alkyl, a 2-halo-acetophenone is treated with an acetone oxime under basic conditions to form the corresponding acetophenone oxime ether H-2. H-2 may be cyclized under acidic conditions, and H-1 may be cyclized under basic conditions to yield the corresponding (substituted 3-alkyl or 3-phenyl)-1,2(2H)-benzisoxazole (I).

For the introduction of the heterocyclic ring A in compounds of the present invention, I may be first functionalized in the 7-position by treatment with n-butyllithium and solid $CO_2$ to provide the carboxylic acid K. Rearrangement of K in the presence of triethylamine and diphenylphosphorylazide forms the corresponding t-butyl 1,2(2H)-benzisoxazolylcarbamate (L). Treatment of L with trifluoroacetic acid affords the aniline M which in turn reacts with trichloromethylchloroformate to give the isocyanate N. Using methods analogous to those described above for Scheme I, cyclization of N provides the pyrimidinedione O which may in turn be converted to III where $R^1$ is either an amino or alkyl group. Examples 4–6 provide details of this procedure.

The construction of the pyrimidinedione ring starting from the anilines E in Scheme 1 and M in Scheme 2 to obtain compounds of formulae II and III of the present invention may also be prepared by the methods described in U.S. Pat. No. 5,169,431, incorporated herein by reference. According to this reference, E may be converted to an alkylcarbamate to give F' where S=NHCO₂-alkyl. F' is treated in generally the same manner as F to obtain G except that the reaction temperature is preferably about 80°–120° C. when using F'. In a similar manner, M may be converted to O via formation of an alkylcarbamate intermediate.

SCHEME 2

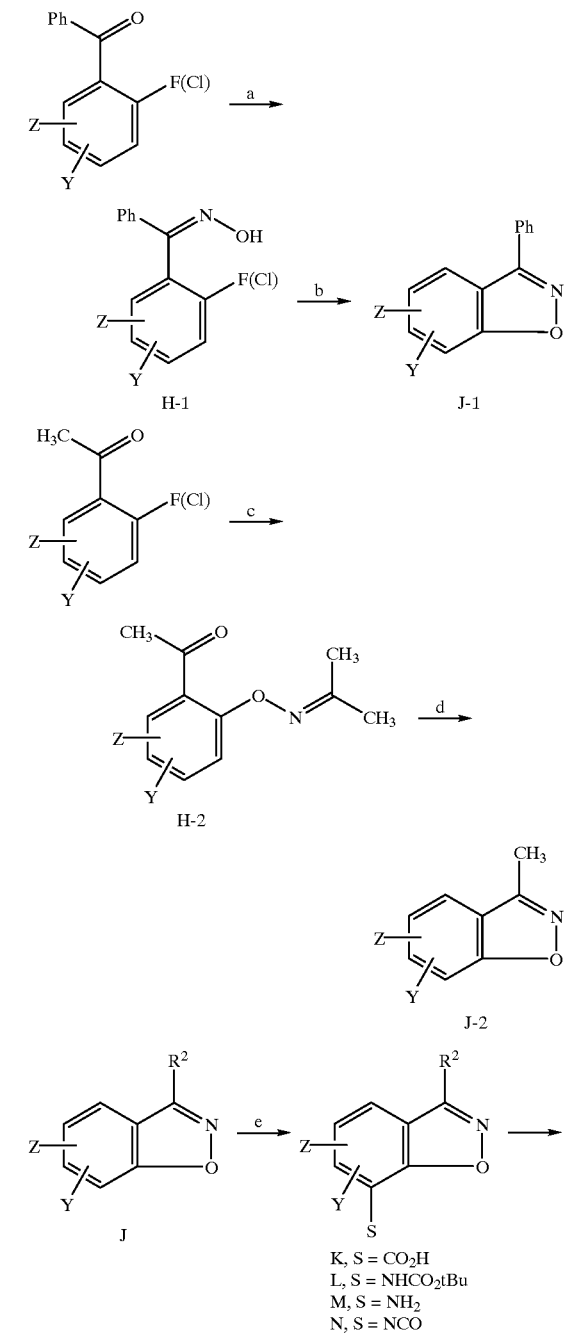

K, S = CO₂H
L, S = NHCO₂tBu
M, S = NH₂
N, S = NCO

-continued

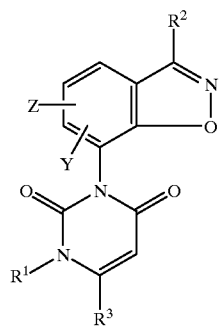

j ⟮ O, R¹ = H, R³ = CF₃
    III, R¹ = alkyl        ⟯ k
    III, R¹ = amino ◄─┘ a) (1) NH₂OH.HCl, Et₃N, (2) tBuOH; (b) EtOH, aq. KOH, warm; (c) acetone oxime, KOtBu, THF; (d) HCl, EtOH, warm; (e) (1) n-BuLi, THF, (2) CO₂, −30 to −50° C.; (f) (1) Et₃N, diphenylphosphorylazide, (2) tBuOH, warm; (g) trifluoroacetic acid; (h) ClCO₂CCl₃, toluene, 80° C.; (i) CF₃C(NH₂)=CHCOCH₂CH₃, NaH, THF, warm; (j) R¹X, K₂CO₃, DMSO, warm; (k) 1-aminooxysulfonyl-2,4,6-trimethylbenzene, K₂CO₃, THF Scheme 3 illustrates a method for the preparation of compounds of the present invention where the heterocyclic ring is a tetrahydrophthalimide. Intermediate E, prepared as described above, undergoes condensation with the anhydride P under acidic conditions to provide IV. Example 7 below provides details of this procedure.

For obtaining compounds of the present invention containing a 1,2,5,6-tetrahydro-1,3,5-triazine-2,6dione ring, compounds E and M above may serve as starting materials followed by triazinedione ring construction according to methods known in the art (e.g., European Patent Application 640 600 A1).

SCHEME 3

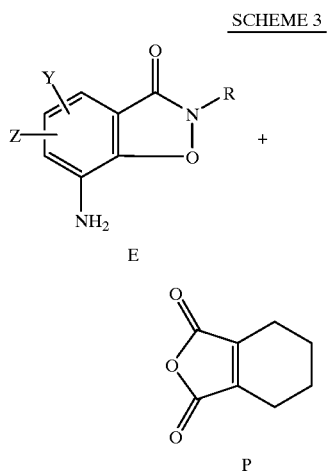

-continued

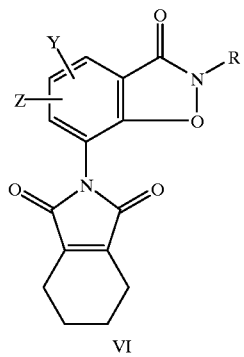

VI

Compounds of the present invention may also be prepared in accordance with the procedures shown in the Examples below, by procedures analogous to those shown in the Examples, or by other methods that are generally known or available to one skilled in the art.

EXAMPLE 1

Synthesis of 3-[4-chloro-2-methyl-1,2(2H)-benzisoxazolidin-3-on-7-yl]-1-methyl-6-trifluoromethyl-2,4(1H,3H)-pyrimidinedione (Compound 2)

Step A N-methyl-N-hydroxy-2-chloro-3-nitrobenzamide

To a stirred solution of 2-chloro-3-nitrobenzoic acid (6.0 grams, 0.031 mole) in toluene (100 mL) was added thionyl chloride (6.8 mL, 0.092 mole). Upon completion of addition, the reaction mixture was heated to reflux where it stirred for four hours. After this time, the reaction mixture was filtered and concentrated. The concentrate was taken up in ether and added dropwise to an ice-cold solution of N-methylhydroxylamine hydrochloride (2.6 g, 0.031 mole), sodium bicarbonate (5.5 g, 0.065 mole), water (20 mL), and ether (160 mL). Upon completion of addition, the reaction mixture was stirred for one hour. After this time, the reaction mixture was diluted with water and the ether layer was separated. The aqueous layer was extracted twice with ether. The combined ether layer and extracts were dried over magnesium sulfate and concentrated to provide 6.4 grams of N-methyl-N-hydroxy-2-chloro-3-nitrobenzamide. The NMR spectrum was consistent with the proposed structure.

Step B 2-methyl-7-nitro-1,2(2H)-benzisoxazolidin-3-one

A stirred solution of N-methyl-N-hydroxy-2chloro-3-nitrobenzamide (6.0 g, 0.026 mole) and DBU (4.0 g, 0.026 mole) in acetonitrile (63 mL) was heated at reflux for 30 minutes. The reaction mixture was concentrated, and the resulting concentrate was partitioned in a mixture of ethyl acetate and water. The mixture was then extracted three times with ethyl acetate. The combined extracts were dried over magnesium sulfate and concentrated. Silica gel column chromatography using 7:3 heptane and ethyl acetate provided 3.0 grams of 2-methyl-7-nitro-1,2(2H)-benzisoxazolidin-3-one. The NMR spectrum was consistent with the proposed structure.

Step C 7-amino-2-methyl-1,2(2H)-benzisoxazolidin-3-one

A stirred solution of 2-methyl-7-nitro-1,2(2)-benzisoxazolidin-3-one (3.3 g, 0.02 mole) in acetic acid (100 mL) and water (15 mL) was heated to 40–45° C., and iron powder (8.0 g, 0.145 mole) was added. Upon completion of addition, the reaction mixture was stirred for two hours at 40–45° C. The reaction mixture was then diluted with water (150 mL) and methylene chloride (150 mL) and allowed to stand at ambient temperature for about 18 hours. After this time, the mixture was filtered through diatomaceous earth and the filter cake washed with methylene chloride. The combined filtrate and washes were placed in a separatory funnel and shaken with an aqueous saturated sodium bicarbonate solution. The organic layer was dried over magnesium sulfate and concentrated to provide 7-amino-2-methyl-1,2(2H)-benzisoxazolidin-3-one. The NMR spectrum was consistent with the proposed structure.

Step D 7-amino-4-chloro-2-methyl-1,2(2H)-benzisoxazoldin-3-one

A stirred solution of 7-amino-2-methyl-1,2(2H)-benzisoxazolidin-3-one (3.3 g, 0.02 mole) in DMF (60 mL) was cooled to −10° C., and a solution of N-chlorosuccinimide (2.7 g, 0.02 mole) in DMF (10 mL) was slowly added. Upon completion of addition, the reaction mixture was warmed to ambient temperature where it stirred for about 18 hours. After this time, the reaction mixture was poured into water, and the mixture was extracted four times with ether. The combined extracts were dried with magnesium sulfate and concentrated. The concentrate was purified by silica gel column chromatography using 1:1 heptane and ethyl acetate to provide 1.4 grams of 7-amino-2-methyl-1,2(2H)-benzisoxazolidin-3-one, m.p. 140–141° C. The NMR spectrum was consistent with the proposed structure.

Step E [4-chloro-2-methyl-1,2(2H)-benzisoxazolidin-3-on-7-yl]isocyanate

To a stirred mixture of 7-amino-4-chloro-2-methyl-1,2 (2H)-benzisoxazolidin-3-one (1.4 g, 0.007 mole) in dioxane (50 mL) was added trichloromethyl chloroformate (1.2 mL, 0.007 mole). The reaction mixture was heated to reflux for 18 hours, and then filtered and concentrated to provide 1.5 grams of 4-chloro-2-methyl-1,2(2H)-benzisoxazolidin-3-on-7-yl]isocyanate.

Step F 3-[4-chloro-2-methyl-1,2(2H)-benzisoxazolidin-3-on-7-yl]-1-methyl-6-trifluoromethyl-2,4(1H,3H)-pyrimidinedione (Compound 2)

A solution of sodium hydride (0.3 g, 0.007 mole, 60% in mineral oil) and ethyl 3-amino-4,4,4-trifluorocrotonate (1.2 g, 0.004 mole) was stirred and cooled to −20° C. in an ice bath. To this solution was slowly added a solution of of 4-chloro-2-methyl-1,2(2H)-benzisoxazolidin-3-on-7-yl] isocyanate (1.5 g, 0.007 mole) in 40 mL of THF. The reaction mixture was then stirred at ambient temperature for one hour, and at reflux for four hours. After this time, the reaction mixture was filtered and concentrated, yielding the sodium salt of 3-[4-chloro-2-methyl-1,2(2H)-benzisoxazolidin-3-on-7-yl]-6-trifluoromethyl-2,4(1H,3H)-pyrimidinedione, m. p. 184–187° C., as a yellow brown solid. The sodium salt was washed with ether, collected by filtration, and then taken up in a solution of methyl iodide (2.8 g, 0.020 mole), potassium carbonate (1.8 g, 0.014 mole), and DMF (60 mL). The reaction mixture was stirred at ambient temperature for about 18 hours, poured into water and extracted with ether. The extract was dried with magnesium sulfate and concentrated, yielding 0.2 gram of Compound 2, m. p. 159–161° C. The NMR spectrum was consistent with the proposed structure.

EXAMPLE 2

Synthesis of 3-[4-bromo-2-methyl-1,2(2H)-benzisoxazolidin-3-on-7-yl]-1-methyl-6-trifluoromethyl-2,4(1H,3H)-pyrimidinedione (Compound 5)

Step A 7-amino-2-methyl-1,2(2H)-benzisoxazolidin-3-one as an intermediate

Under a nitrogen atmosphere, a solution of 5-bromo-2-methyl-7-nitro-1,2(2H)-benzisoxazolidin-3-one (10.4 g, 0.043 mole) in ethanol (200 mL) was hydrogenated in a Parr apparatus in the presence of 10% Palladium on carbon (0.03 gram) in dioxane (0.50 mL). The reaction mixture was filtered and concentrated whereupon the residue was dissolved in ethyl acetate and neutralized with sodium bicarbonate. The organic layer separated and the aqueous layer was extracted twice with ethyl acetate. The combined organic layer and extracts were dried with magnesium sulfate and concentrated, yielding 10.0 grams of a reddish brown solid. The solid was subjected to silica gel column chromatography using 1:1 heptane and ethyl acetate, followed by pure ethyl acetate. Starting material was recovered as determined by the NMR and IR spectra. As a result, the above hydrogenation was repeated using 0.40 g of 10% Palladium on carbon, 200 mL of ethanol, and 30 mL of acetic acid. After about seven hours of hydrogenation, the reaction mixture was analyzed by TLC, which indicated the reaction had not gone to completion. The reaction mixture stood for about 18 hours, then an additional 0.30 gram of 10% Palladium on carbon was added to the reaction mixture. The hydrogenation continued for 2.5 hours. The reaction mixture was then analyzed by TLC, which indicated the reaction was complete. The product was isolated from the reaction mixture in the manner stated above, yielding 6.0 grams of 7-amino-2-methyl-1,2(2H)-benzisoxazolidin-3one. The NMR spectrum was consistent with the proposed structure.

Step B 7-amino-4-bromo-2-methyl-1,2(2H)-benzisoxazolidin-3-one

This compound was prepared in the manner of Step D, Example 1, using 7-amino-2-methyl-1,2(2H)-benzisoxazolidin-3-one (2.2 g, 0.014 mole), DMF (50 mL) and N-bromosuccinimide (2.7 g, 0.015 mole). The yield of 7-amino4-bromo-2-methyl-1,2(2H)-benzisoxazolidin-3-one was 2.5 grams. The NMR spectrum was consistent with the proposed structure.

Step C [4-bromo-2-methyl-1,2(2H)-benzisoxazolidin-3-on-7-yl]isocyanate

This compound was prepared in the manner of Step E, Example 1, using 7-amino-4-bromo-2-methyl-1,2(2H)-benzisoxazolidin-3-one (2.2 g, 0.009 mole), toluene (100 mL), trichloromethyl chloroformate (1.8 g, 0.009 mole), and dioxane (30 mL). The yield of [4-bromo-2-methyl-1,2(2H)-benzisoxazolidin-3-on-7-yl]isocyanate was about 2.4 grams. The IR spectrum was consistent with the proposed structure.

Step D 3-[4-bromo-2-methyl-1,2(2H)-benzisoxazolidin-3-on-7-yl]-1-methyl-6-trifluoromethyl-2,4(1H,3H)-pyrimidinedione (Compound 5)

This compound was prepared in the manner of Step F, Example 1, using sodium hydride (0.43 g, 0.011 mole, 60% in mineral oil), ethyl 3-amino-4,4,4-trifluorocrotonate (1.6 g, 0.009 mole), THF (80 mL), [4-bromo-2-methyl-1,2(2H)-benzisoxazolidin-3-on-7-yl]isocyanate (2.4 g, 0.009 mole), methyl iodide (1.5 g, 0.011 mole), potassium carbonate (1.5 g, 0.011 mole), and dimethyl sulfoxide (15 mL). The yield of Compound 5 was 0.85 gram, m.p. 201–203.5° C. The NMR spectrum was consistent with the proposed structure.

EXAMPLE 3

Synthesis of 3-[4-bromo-2-isopropyl-1,2(2H)-benzisoxazolidin-3-on-7-yl]-1-amino-6-trifluoromethyl-2,4(1H,3H)-pyrimidinedione (Compound 11)

A solution of 3-[4-bromo-2-isopropyl-1,2(2H)-benzisoxazolidin-3-on-7-yl]-6-trifluoromethyl-2,4(1H,3H)-pyrimidinedione (1.1 g, 0.002 mole), 1-aminooxysulfonyl- 2,4,6-trimethylbenzene (0.5 g, 0.002 mole), potassium carbonate (0.4 g, 0.003 mole), and THF (15 mL) was stirred at ambient temperature for 18 h. The reaction was diluted with water and extracted with ethyl acetate (3×50 mL). The combined extracts were dried over magnesium sulfate and concentrated. Silica gel chromatography using heptane and ethyl acetate provided 0.5 gram of Compound 11. The NMR spectrum was consistent with the proposed structure.

EXAMPLE 4

Synthesis of 3-[4-chloro-6-fluoro-3-methyl-1,2(2H)-benzisoxazol-7-yl]-1-methyl-6-trifluoromethyl-2,4 (1H,3H)-pyrimidinedione (Compound 27)

Step A 2-(2-propyliminooxy)-4-fluoroacetophenone

A mixture of potassium t-butoxide (9.0 g, 0.08 mole) and of acetone oxime (5.9 g, 0.08 mole) in THF (50 mL) was stirred for one hour. The mixture was added dropwise to a solution of 2,4-difluoroacetophenone (13.7 g, 0.08 mole) in THF (50 mL) during a one minute period. Upon completion of addition, the reaction mixture was stirred for 30 minutes. The reaction mixture was then poured into an aqueous saturated ammonium chloride solution. The mixture was extracted with ether, and the extract was washed with water. The extract was dried with magnesium sulfate and concentrated to a residue. The residue was subjected to silica gel column chromatography using hexane and methylene chloride. The chromatographed product (18.3 g) was recrystallized from hexane, yielding 8.2 grams of 2-(2-propyliminooxy)-4-fluoroacetophenone, m.p. 57–58° C. The NMR spectrum was consistent with the proposed structure.

Step B 6-fluoro-3-methyl-1,2(2H)-benzisoxazole

A stirred solution of 2-(2-propyliminooxy)-4-fluoroacetophenone (7.8 g, 0.037 mole), aqueous 1 N HCl (30 mL), and ethanol (30 mL) was heated at reflux for three hours. After this time, the reaction mixture was poured into water and thoroughly extracted with ether. The combined extracts were washed with water. The organic layer was dried with magnesium sulfate and concentrated, yielding 5.5 grams of 6-fluoro-3-methyl-1,2(2H)-benzisoxazole. The NMR spectrum was consistent with the proposed structure.

Step C [6-fluoro-3-methyl-1,2(2H)-benzisoxazol-7-yl] carboxylic acid

A stirred solution of 6-fluoro-3-methyl-1,2(2H)-benzisoxazole (5.5 g, 0.037 mole) in THF (100 mL) was cooled in a dry ice-acetone bath, and 2.5 M n-butyllithium in hexanes (16 mL, 0.040 mole) was added dropwise. Upon completion of addition, the reaction mixture was stirred for one hour. The reaction mixture was then exposed to a $CO_2$ atmosphere where it stirred for three hours. After this time, the reaction mixture was poured into water. The mixture was washed with ether, acidified with hydrochloric acid, and then extracted repeatedly with ether. The combine extracts were washed with water, dried with magnesium sulfate and concentrated yielding 4.5 grams of [6-fluoro-3-methyl-1,2(2H)-benzisoxazol-7-yl]carboxylic acid. The NMR spectrum was consistent with the proposed structure.

Step D t-butyl N-(6-fluoro-3-methyl-1,2(2H)-benzisoxazol-7-yl)carbamate and 7-amino-6-fluoro-3-methyl-1,2(2H)-benzisoxazole A stirred solution of [6-fluoro-3-methyl-1,2(2H)-benzisoxazol-7-yl]carboxylic acid (5.3 g, 0.027 mole), diphenylphosphoryl azide (7.4 g, 0.027 mole), and triethylamine (2.7 g, 0.027 mole) in t-butyl alcohol (100 mL) was heated at reflux for about 72 hours. After this time, the reaction mixture was concentrated to a residue. The residue was subjected to silica gel column chromatography using 9:1 to 1:1 hexane and ethyl acetate. The fractions containing t-butyl N-(6-fluoro-3-methyl-1,2(2H)-benzisoxazol-7-yl) carbamate were combined and concentrated, yielding 3.7 grams of that product, m.p. 121–123° C. The fractions containing 7-amino-6-fluoro-3-methyl-1,2(2H)-benzisoxazole were combined and concentrated, yielding 1.4 grams of that product. The NMR spectra were consistent with the proposed structures.

Step E 7-amino-6-fluoro-3-methyl-1,2(2H)-benzisoxazole

Trifluoroacetic acid (50 mL) was stirred and cooled in an ice-water bath. To this was added t-butyl N-(6-fluoro-3-methyl-1,2(2H)-benzisoxazol-7-yl)carbamate (3.0 g). Upon completion of addition, the reaction mixture was stirred for one hour and then concentrated to a residue. The residue was taken up in water and made basic to pH 8 with sodium bicarbonate. The mixture was then extracted thoroughly with methylene chloride. The combined extracts were washed with water, dried with magnesium sulfate, and concentrated, yielding 2.1 grams of 7-amino-6-fluoro-3-methyl-1,2(2H)-benzisoxazole. The NMR spectrum was consistent with the proposed structure.

Step F 7-amino-4-chloro-6-fluoro-3-methyl-1,2(2H)-benzisoxazole

A solution of 7-amino-6-fluoro-3-methyl-1,2(2H)-benzisoxazole (3.5 g, 0.021 mole) in DMF (50 mL) was stirred, and a solution of N-chlorosuccinimide (2.8 g, 0.02 mole) in a minimum amount of DMF was added dropwise. Upon completion of addition, the reaction mixture was stirred for about 18 hours. After this time, the reaction mixture was poured into aqueous 10% lithium chloride and then thoroughly extracted with ether. The combined extracts were washed with aqueous 10% lithium chloride, dried with magnesium sulfate, and concentrated to a residue. The residue was subjected to silica gel column chromatography using 9:1 to 4:1 hexane and ethyl acetate to provide 2.6 grams of 7-amino-4-chloro-6-fluoro-3-methyl-1,2(2H)-benzisoxazole. The NMR spectrum was consistent with the proposed structure.

Step G 3-[4-chloro-6-fluoro-3-methyl-1,2(2H)-benzisoxazol-7-yl]-6-trifluoromethyl-2,4(1H,3H)-pyrimidinedione Trichloromethylchloroformate (2.5 g, 0.013 mole) was added dropwise to a stirred solution of 7-amino-4-chloro-6-fluoro-3-methyl-1,2(2H)-benzisoxazole (2.6 g, 0.013 mole) in toluene (50 mL). Upon completion of addition, the reaction mixture was heated to 80° C. where it stirred for about 18 hours. After this time, the reaction mixture was concentrated to provide 3-[4-chloro-6-fluoro-3-methyl-1,2 (2H)-benzisoxazol-7-yl]isocyanate. In a separate reaction vessel, sodium hydride (0.8 g, 0.019 mole, 60% in mineral oil) was washed twice with heptane, and then taken up in THF (100 mL). The stirred mixture was cooled to −20° C., and a solution of ethyl 3-amino-4,4,4-trifluorocrotonate (2.5 g, 0.013 mole) in a minimum amount of THF was added dropwise. Upon completion of addition, the reaction mixture was stirred for 10 minutes, and then a solution of the above isocyanate in a minimum amount of THF was added. The reaction mixture was allowed to warm to ambient temperature, and was then heated to just below reflux were it stirred for about 18 hours. After this time, the reaction mixture was concentrated to a residue, and water was added. The resultant solution was washed with ether and acidified with concentrated hydrochloric acid. The mixture was thoroughly extracted with ether and the extracts washed with water. The organic layer was separated, dried with magnesium sulfate, and concentrated to a solid residue. The residue was subjected to silica gel column chromatography using 9:1 to 1:1 hexane and ethyl acetate, providing 4.1 grams of 3-[4-chloro-6-fluoro-3-methyl-1,2(2H)-benzisoxazol-7-yl]-6-trifluoromethyl-2,4(1H,3H)-pyrirndinedione. The NMR spectrum was consistent with the proposed structure.

Step H 3-[4-chloro-6-fluoro-2-methyl-1,2(2H)-benzisoxazol-7-yl]-1-methyl-6-trifluoromethyl-2,4(1H,3H)-pyrimidinedione (Compound 27)

A solution of 3-[4-chloro-6-fluoro-3-methyl-1,2(2H)-benzisoxazol-7-yl]-6-trifluoromethyl-2,4(1H,3H)-pyrimidinedione (3.5 g, 0.010 mole), methyl iodide (2.1 g, 0.014 mole), potassium carbonate (2.0 g, 0.003 mole), and THF (100 mL) was heated to reflux where it stirred for five hours. The reaction mixture was then cooled to ambient temperature where it stirred for about 72 hours. After this time, the reaction mixture was poured into water and thoroughly extracted with ether. The combined extracts were washed with water and an aqueous saturated sodium chloride solution. The organic layer was separated, dried with magnesium sulfate, and concentrated to a residue. The residue was subjected to silica gel column chromatography using 9:1 to 5:1 hexane and ethyl acetate. The product-containing fractions provided 2.0 grams of Compound 27, m.p. 218–219° C. The NMR spectrum was consistent with the proposed structure.

EXAMPLE 5

Synthesis of 3-[4-chloro-6-fluoro-3-phenyl-1,2(2H)-benzisoxazol-7-yl]-1-amino-6-trifluoromethyl-2,4 (1H,3H)-pyrimidinedione (Compound 34)

1-Aminooxysulfonyl-2,4,6-trimethylbenzene (0.5 g, 0.002 mole) was added all at once to a stirred solution of 3-[4-chloro-6-fluoro-3-phenyl-1,2(2H)-benzisoxazol-7-yl]-6-trifluoromethyl-2,4(1H,3H)-pyrimidinedione (0.8 g, 0.002 mole) and potassium carbonate (0.4 g, 0.003 mole) in THF (50 mL). Upon completion of addition, the reaction mixture was stirred at ambient temperature for about 18 hours. After this time, the reaction mixture was filtered and the filtrate was concentrated to a residue. The residue was subjected to silica gel column chromatography using 4:1 hexane and ethyl acetate. The product-containing fractions were combined and concentrated, yielding 0.6 gram of Compound 34, m.p. 171–173° C. The NMR spectrum was consistent with the proposed structure.

EXAMPLE 6

Synthesis of 3-[4-chloro-6-fluoro-3-phenyl-1,2(2H)-benzisoxazol-7-yl]-1-methyl-6-trifluoromethyl-2,4 (1H,3H)-pyrimidinedione (Compound 31)

This compound was prepared in the manner of Step H, Example 4, using 3-[4-chloro-6-fluoro-3-phenyl-1,2(2H)-benzisoxazol-7-yl]-6-trifluoromethyl-2,4(1H,3H)-pyrimidinedione (0.8 g, 0.002 mole), methyl iodide (0.03 g, 0.002 mole), potassium carbonate (0.5 g, 0.004 mole), and THF (50 mL). The yield of Compound 31 was 0.5 gram. The NMR spectrum was consistent with the proposed structure.

EXAMPLE 7

Synthesis of 4,5,6,7-tetrahydro-2-[4-bromo-2-isopropyl-1,2(2H)-benzisoxazolidin-3-on-7-yl]-1H-isoindole-1,3(2H)-dione (Compound 62)

A stirred solution of 7-amino-4-bromo-2-isopropyl-1,2 (2H)-benzisoxazolidin-3-one (0.13 g, 0.0005 mole) and 4,5,6,7-tetrahydro-1,3-isobenzofurandione (0.072 g, 0.0005 mole) in glacial acetic acid (40 mL) was heated to reflux where it stirred for 18 hours. After this time, the reaction mixture was poured into water, and the resulting solution was extracted three times with ether. The combined extracts were dried with magnesium sulfate and concentrated to a residue. This residue was subjected to silica gel column chromatography using methylene chloride, providing 0.08 gram of Compound 62, m.p. 115–116° C. The NMR spectrum was consistent with the proposed structure.

TABLE 1

Representative Compounds of the Present Invention

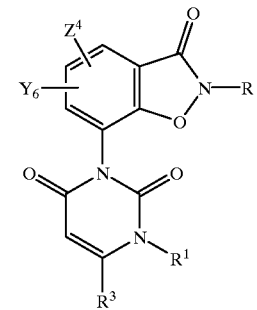

| Compd No. | R | R¹ | Y | Z | R³ |
|---|---|---|---|---|---|
| 1 | —CH₃ | —CH₃ | H | H | —CF₃ |
| 2 | —CH₃ | —CH₃ | 4-Cl | H | —CF₃ |
| 3 | —CH₃ | —CH₃ | H | 6-Cl | —CF₃ |
| 4 | —CH₃ | —CH₃ | 4-Cl | 6-Cl | —CF₃ |
| 5 | —CH₃ | —CH₃ | 4-Br | H | —CF₃ |
| 6 | —CH₃ | —CH₃ | H | 5-Br | —CF₃ |
| 7 | —CH(CH₃)₂ | —CH₃ | H | H | —CF₃ |
| 8 | —CH(CH₃)₂ | —CH₃ | 4-Cl | H | —CF₃ |
| 9 | —CH(CH₃)₂ | —CH₃ | 4-Cl | 6-Cl | —CF₃ |
| 10 | —CH(CH₃)₂ | —CH₃ | 4-Br | H | —CF₃ |
| 11 | —CH(CH₃)₂ | —NH₂ | 4-Br | H | —CF₃ |
| 12 | —CH₃ | —CH₃ | 4-Cl | 6-F | —CF₃ |
| 13 | —CH₃ | —NH₂ | 4-Cl | 6-F | —CF₃ |
| 14 | —C₂H₅ | —CH₃ | 4-Cl | H | —CF₃ |
| 15 | —CH₂CH₂CH₃ | —CH₃ | 4-Cl | H | —CF₃ |
| 16 | —CH₂CH(CH₃)CH₂CH₃ | —CH₃ | 4-Cl | H | —CF₃ |
| 17 | —CH₃ | —CH₃ | 4-CN | H | —CF₃ |
| 18 | —CH₃ | —CH₃ | 4-CF₃ | H | —CF₃ |
| 19 | —CH₂CH=CH₂ | —CH₃ | 4-Cl | H | —CF₃ |
| 20 | —C(CH₃)₄ | —CH₃ | 4-Cl | H | —CF₃ |
| 21 | —CH₂CO₂CH₃ | —CH₃ | 4-Cl | 6-F | —CF₃ |
| 22 | —CH₂CH₂CO₂CH₃ | —CH₃ | 4-Cl | 6-F | —CF₃ |
| 23 | —CH₂CHClCO₂CH₃ | —CH₃ | 4-Cl | 6-F | —CF₃ |
| 24 | —CH₂C₆H₅ | —CH₃ | 4-Cl | 6-F | —CF₃ |
| 25 | —C₆H₅ | —CH₃ | 4-Cl | 6-F | —CF₃ |
| 26 | —CH₂CN | —CH₃ | 4-Cl | 6-F | —CF₃ |

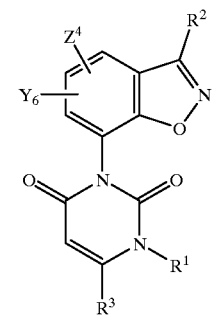

| Cmpd. No. | R¹ | R² | Y | Z | R³ |
|---|---|---|---|---|---|
| 27 | —CH₃ | —CH₃ | 4-Cl | 6-F | —CF₃ |
| 28 | —CH₃ | —CH₃ | 4-Cl | 6-Cl | —CF₃ |
| 29 | —NH₂ | —CH₃ | 4-Cl | 6-Cl | —CF₃ |
| 30 | —CH₃ | phenyl | H | 6-F | —CF₃ |

TABLE 1-continued

Representative Compounds of the Present Invention

| | | | | | |
|---|---|---|---|---|---|
| 31 | —$CH_3$ | phenyl | 4-Cl | 6-F | —$CF_3$ |
| 32 | —$CH_3$ | phenyl | 4-Br | 6-F | —$CF_3$ |
| 33 | —$NH_2$ | phenyl | H | 6-F | —$CF_3$ |
| 34 | —$NH_2$ | phenyl | 4-Cl | 6-F | —$CF_3$ |
| 35 | —$CH_3$ | —$C_2H_5$ | 4-Cl | H | —$CF_3$ |
| 36 | —$CH_3$ | —$C_3H_7$ | 4-Cl | H | —$CF_3$ |
| 37 | —$CH_3$ | —$CH(CH_3)_2$ | 4-Cl | H | —$CF_3$ |
| 38 | —$CH_3$ | —$CF_3$ | 4-Cl | H | —$CF_3$ |
| 39 | —$CH_3$ | Cl | 4-Cl | H | —$CF_3$ |
| 40 | —$CH_3$ | —$CO_2CH_3$ | 4-Cl | H | —$CF_3$ |
| 41 | —$CH_3$ | 4-chlorophenyl | 4-Cl | H | —$CF_3$ |
| 42 | —$CH_3$ | 4-tolyl | 4-Cl | H | —$CF_3$ |
| 43 | —$CH_3$ | 2,4-dichlorophenyl | 4-Cl | H | —$CF_3$ |
| 44 | —$CH_3$ | 4-fluorophenyl | 4-Cl | H | —$CF_3$ |
| 45 | —$CH_3$ | —$OCH_2CO_2CH_3$ | 4-Cl | 6-F | —$CF_3$ |
| 46 | —$CH_3$ | —$OCH(CH_3)CO_2CH_3$ | 4-Cl | 6-F | —$CF_3$ |
| 47 | —$CH_3$ | —$OCH_2CN$ | 4-Cl | 6-F | —$CF_3$ |
| 48 | —$CH_3$ | —$OCH_3$ | 4-Cl | 6-F | —$CF_3$ |
| 49 | —$CH_3$ | —$OCH(CH_3)_2$ | 4-Cl | 6-F | —$CF_3$ |
| 50 | —$CH_3$ | —$OCH_2C_6H_5$ | 4-Cl | 6-F | —$CF_3$ |

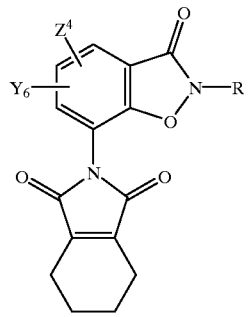

| Cmpd. No. | R | Y | Z |
|---|---|---|---|
| 51 | —$CH_3$ | H | H |
| 52 | —$CH_3$ | 4-Cl | H |
| 53 | —$CH_3$ | 4-Br | H |
| 54 | —$CH_3$ | 4-CN | H |
| 55 | —$CH_3$ | 4-$CF_3$ | H |
| 56 | —$CH_3$ | H | 6-Cl |
| 57 | —$CH_3$ | H | 5-Br |
| 58 | —$CH_3$ | 4-Cl | 6-Cl |
| 59 | —$CH_3$ | 4-Cl | 6-F |
| 60 | —$CH(CH_3)_2$ | H | H |
| 61 | —$CH(CH_3)_2$ | 4-Cl | H |
| 62 | —$CH(CH_3)_2$ | 4-Br | H |
| 63 | —$CH(CH_3)_2$ | 4-Cl | 6-Cl |
| 64 | —$C_2H_5$ | 4-Cl | H |
| 65 | —$CH_2CH_2CH_3$ | 4-Cl | H |
| 66 | —$CH_2CH(CH_3)CH_2CH_3$ | 4-Cl | H |
| 67 | —$CH_2CH=CH_2$ | 4-Cl | H |
| 68 | —$C(CH_3)_4$ | 4-Cl | H |
| 69 | —$CH_2CO_2CH_3$ | 4-Cl | 6-F |
| 70 | —$CH_2CH_2CO_2CH_3$ | 4-Cl | 6-F |
| 71 | —$CH_2CHClCO_2CH_3$ | 4-Cl | 6-F |
| 72 | —$CH_2C_6H_5$ | 4-Cl | 6-F |
| 73 | —$C_6H_5$ | 4-Cl | 6-F |
| 74 | —$CH_2CN$ | 4-Cl | 6-F |

TABLE 1-continued

Representative Compounds of the Present Invention

| Compd No. | R | $R^1$ | Y | Z | $R^3$ |
|---|---|---|---|---|---|
| 75 | —$CH_3$ | —$CH_3$ | H | H | —$CF_3$ |
| 76 | —$CH_3$ | —$CH_3$ | 4-Cl | H | —$CF_3$ |
| 77 | —$CH_3$ | —$CH_3$ | H | 6-Cl | —$CF_3$ |
| 78 | —$CH_3$ | —$CH_3$ | 4-Cl | 6-Cl | —$CF_3$ |
| 79 | —$CH_3$ | —$CHF_2$ | 4-Cl | H | —$CH_3$ |
| 80 | —$CH_3$ | —$NH_2$ | H | 6-Cl | —$CF_3$ |
| 81 | —$CH(CH_3)_2$ | —$CH_3$ | H | H | —$CF_3$ |
| 82 | —$CH(CH_3)_2$ | —$CH_3$ | 4-Cl | H | —$CF_3$ |
| 83 | —$CH(CH_3)_2$ | —$CH_3$ | 4-Cl | 6-F | —$CF_3$ |

TABLE 2

Empirical Formula and Characterizing Data for Representative Compounds

| Cmpd No | Empirical Formula | Melting Point (° C.) or Physical State |
|---|---|---|
| 1 | $C_{14}H_{10}F_3N_3O_4$ | 177.5–179 |
| 2 | $C_{14}H_9ClF_3N_3O_4$ | 159–161 |
| 3 | $C_{14}H_9ClF_3N_3O_4$ | 95–97.5 |
| 4 | $C_{14}H_8Cl_2F_3N_3O_4$ | SOLID |
| 5 | $C_{14}H_9BrF_3N_3O_4$ | 201–203.5 |
| 6 | $C_{14}H_9BrF_3N_3O_4$ | OIL |
| 7 | $C_{16}H_{14}F_3N_3O_4$ | 106–109 |
| 8 | $C_{16}H_{13}ClF_3N_3O_4$ | 147–148 |
| 9 | $C_{16}H_{12}Cl_2F_3N_3O_4$ | SOLID |
| 10 | $C_{16}H_{13}BrF_3N_3O_4$ | 147–149 |
| 11 | $C_{15}H_{12}BrF_3N_4O_4$ | OIL |
| 27 | $C_{14}H_8ClF_4N_3O_3$ | 218–219 |
| 28 | $C_{14}H_8C_{12}F_3N_3O_3$ | 143–146 |
| 29 | $C_{13}H_7Cl_2F_3N_4O_3$ | 174–176 |
| 30 | $C_{19}H_{11}F_4N_3O_3$ | 210–211 |
| 31 | $C_{19}H_{10}ClF_4N_3O_3$ | OIL |
| 32 | $C_{19}H_{10}BrF_4N_3O_3$ | OIL |
| 33 | $C_{18}H_{10}F_4N_4O_3$ | 226–227 |
| 34 | $C_{18}H_9ClF_4N_4O_3$ | SOLID PASTE |
| 62 | $C_{18}H_{17}BrN_2O_4$ | 115–116 |

HERBICIDAL ACTIVITY

The compounds of the present invention were tested for pre- and post-emergence herbicidal activity using a variety of crops and weeds. The test plants included soybean (*Glycine max* var. Winchester), field corn (*Zea mays* var. Pioneer 3732), wheat (*Triticum aestivum* var. Lew), morning glory (*Ipomea lacunosa* or *Ipomea hederacea*), velvetleaf (*Abutilon theophrasti*), green foxtail (*Setaria viridis*), Johnsongrass (*Sorghum halepense*), blackgrass (*Aloepecurus myosuroides*), common chickweed (*Stellaria media*), and common cocklebur (*Xanthium strumarium* L.).

For pre-emergence testing, two disposable fiber flats (8 cm×15 cm×25 cm) for each rate of application of each candidate herbicide were filled to an approximate depth of 6.5 cm with steam-sterilized sandy loam soil. The soil was leveled and impressed with a template to provide five evenly spaced furrows 13 cm long and 0.5 cm deep in each flat. Seeds of soybean, wheat, corn, green foxtail, and johnsongrass were planted in the furrows of the first flat, and seeds of velvetleaf, morningglory, common chickweed, cocklebur, and blackgrass were planted in the furrows of the second flat. The five-row template was employed to firmly press the seeds into place. A topping soil of equal portions of sand and sandy loam soil was placed uniformly on top of each flat to a depth of approximately 0.5 cm. Flats for post-emergence testing were prepared in the same manner except that they were planted 9–14 days prior-to the pre-emergence flats and were placed in a greenhouse and watered, thus allowing the seeds to germinate and the foliage to develop.

In both pre- and post-emergence tests, a stock solution of the candidate herbicide was prepared by dissolving 0.27 g of the compound in 20 mL of water/acetone (50/50) containing 0.5% v/v sorbitan monolaurate. For an application rate of 3000 g/ha of herbicide a 10 mL portion of the stock solution was diluted with water/acetone (50/50) to 45 mL. The volumes of stock solution and diluent used to prepare solutions for lower application rates are shown in the following table:

| Application Rate (g/ha) | Volume of Stock Solution (mL) | Volume of Acetone/Water (mL) | Total Volume of Spray Solution (mL) |
|---|---|---|---|
| 3000 | 10 | 35 | 45 |
| 1000 | 3 | 42 | 45 |
| 300 | 1 | 44 | 45 |
| 100 | 0.3 | 45 | 45.3 |
| 30 | 0.1 | 45 | 45.1 |
| 10 | 0.03 | 45 | 45.03 |
| 3 | 0.01 | 45 | 45.01 |

The pre-emergence flats were initially subjected to a light water spray. The four flats were placed two by two along a conveyor belt (i.e., the two pre-emergence flats, followed by the two post-emergence flats). The conveyor belt fed under a spray nozzle mounted about ten inches above the post-emergent foliage. The pre-emergent flats were elevated on the belt so that the soil surface was at the same level below the spray nozzle as the foliage canopy of the post-emergent plants. After the spray of herbicidal solution was commenced and stabilized, the flats were passed under the spray at a speed to receive a coverage equivalent to 1000 L/ha. At this coverage, the application rates are those shown in the above table for the individual herbicidal solutions. The pre-emergence flats were watered immediately thereafter, placed in the greenhouse, and watered regularly at the soil surface. The post-emergence flats were immediately placed in the green-house, but not watered until 24 hours after treatment with the test solution. Thereafter, they were regularly watered at ground level. After 12–17 days, the plants were examined, and the phytotoxicity data were recorded.

Herbicidal activity data at selected application rates are given for various compounds of the present invention in Tables 3 and 4. The test compounds are identified by numbers which correspond to those in Table 1.

Phytotoxicity data are taken as percent control. Percent control is determined by a method similar to the 0 to 100 rating system disclosed in "Research Methods in Weed Science," 2nd ed., B. Truelove, Ed. (Southern Weed Science Society; Auburn University, Auburn, Ala., 1977). The rating system is as follows:

| Rating (% Control) | Description of Main Categories | Crop Description | Weed Description |
|---|---|---|---|
| 0 | No Effect | No crop reduction or injury | No weed control |
| 10 | Slight Effect | Slight discoloration or stunting | Very poor weed control |
| 20 | | Some discoloration, stunting or stand loss | Poor weed control |
| 30 | | Crop injury more pronounced, but not lasting | Poor to deficient weed control |
| 40 | Moderate Effect | Moderate injury, crop usually recovers | Deficient weed control |
| 50 | | Crop injury more lasting, recovery doubtful | Deficient to moderate weed control |
| 60 | | Lasting crop injury, no recovery | Moderate weed control |
| 70 | Severe | Heavy injury and stand loss | Control somewhat less than satisfactory |
| 80 | | Crop nearly destroyed, a few survivors | Satisfactory to good weed control |
| 90 | | Only occasional live plants left | Very good to excellent control |
| 100 | Complete Effect | Complete crop destruction | Complete weed destruction |

TABLE 3

Pre-emergence Herbicidal Activity (% Control)

| Cmpd. No. | Rate | Soybean | Wheat | Corn | ABUTH | IPOSS | STEME | XANPE |
|---|---|---|---|---|---|---|---|---|
| 1 | 0.3 | 100 | 80 | 95 | 100 | 100 | 100 | 100 |
| 2 | 0.3 | 100 | 100 | 100 | 100 | 100 | 100 | 100 |
| 3 | 1.0 | 100 | 90 | 100 | 100 | 100 | 100 | 95 |
| 4 | 1.0 | 100 | 100 | 100 | 100 | 100 | 100 | 100 |
| 5 | 0.1 | 100 | 100 | 100 | 100 | 100 | 100 | 100 |
| 7 | 0.1 | 100 | 100 | 100 | 100 | 100 | 100 | 100 |
| 8 | 0.3 | 100 | 100 | 95 | 100 | 100 | 100 | 100 |
| 9 | 1.0 | 100 | 100 | 100 | 100 | 100 | 100 | 100 |
| 10 | 0.3 | 100 | 100 | 100 | 100 | 100 | 100 | 100 |
| 11 | 0.3 | 100 | 100 | 100 | 100 | 100 | 100 | 100 |
| 27 | 1.0 | 70 | 60 | 70 | 100 | 100 | 100 | 60 |
| 28 | 1.0 | 40 | 20 | 50 | 95 | 40 | 20 | 30 |
| 29 | 1.0 | 50 | 30 | 50 | 100 | 70 | 30 | 30 |
| 30 | 1.0 | 0 | 20 | 10 | 50 | 0 | 10 | 0 |
| 31 | 3.0 | 10 | 0 | 10 | 80 | 60 | 50 | 10 |
| 32 | 3.0 | 50 | 0 | 30 | 95 | 95 | 60 | 70 |
| 33 | 1.0 | 30 | 20 | 50 | 30 | 50 | 60 | 50 |
| 34 | 3.0 | 50 | 5 | 40 | 90 | 90 | 70 | 20 |

Rate is in kg/hectare.
ABUTH is velvetleaf;
IPOSS, morningglory;
STEME, chickweed;
XANPE, cocklebur;
ALOMY, blackgrass;
SETVI, green foxtail;
SORHA, johnsongrass

TABLE 4

Post-emergence Herbicidal Activity (% Control)

| Cmpd. No. | Rate | Soybean | Wheat | Corn | ABUTH | IPOSS | STEME | XANPE |
|---|---|---|---|---|---|---|---|---|
| 1 | 0.3 | 95 | 60 | 80 | 100 | 100 | 100 | 100 |
| 2 | 0.3 | 100 | 100 | 100 | 100 | 100 | 100 | 100 |
| 3 | 1.0 | 95 | 40 | 80 | 100 | 95 | 20 | 70 |
| 4 | 1.0 | 100 | 100 | 100 | 100 | 100 | 100 | 100 |
| 5 | 0.1 | 95 | 60 | 80 | 100 | 100 | 100 | 100 |
| 7 | 0.1 | 100 | 70 | 90 | 100 | 100 | 100 | 100 |
| 8 | 0.3 | 100 | 100 | 100 | 100 | 100 | 100 | 100 |
| 9 | 1.0 | 100 | 100 | 100 | 100 | 100 | 100 | 100 |
| 10 | 0.3 | 100 | 100 | 100 | 100 | 100 | 100 | 100 |
| 11 | 0.3 | 100 | 100 | 100 | 100 | 100 | 100 | 100 |
| 27 | 1.0 | 95 | 65 | 70 | 100 | 100 | 100 | 100 |
| 28 | 1.0 | 70 | 40 | 65 | 100 | 90 | 5 | 30 |
| 29 | 1.0 | 70 | 50 | 65 | 100 | 90 | 0 | 60 |
| 30 | 1.0 | 20 | 20 | 15 | 60 | 40 | 0 | 0 |
| 31 | 3.0 | 60 | 5 | 50 | 95 | 100 | 30 | ND |
| 32 | 3.0 | 60 | 15 | 60 | 100 | 100 | 50 | 100 |
| 33 | 1.0 | 50 | 5 | 25 | 60 | 40 | 0 | 20 |
| 34 | 3.0 | 60 | 40 | 55 | 100 | 100 | 60 | ND |

Rate is in kg/hectare.
ABUTH is velvetleaf;
IPOSS, morningglory;
STEME, chickweed;
XANPE, cocklebur;
ALOMY, blackgrass;
SETVI, green foxtail;
SORHA, johnsongrass Herbicidal compositions are prepared by combining herbicidally effective amounts of the active compounds with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application. It is to be understood that the amounts specified in this specification are intended to be approximate only, as if the word "about" were placed in front of the amounts specified.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and post-emergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.0 parts of the herbicidal compound, 17.9 parts of Palmetto clay, and 1.0 part of sodium lignosulfonate and 0.3 part of sulfonated aliphatic polyester as wetting agents. Additional wetting agent and/or oil will frequently be added to the tank mix for post-emergence application to facilitate dispersion on the foliage and absorption by the plant.

Other useful formulations for herbicidal applications are emulsifiable concentrates (ECs) which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isphorone, or other non-volatile organic solvents. For herbicidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, e.g. about 1 to 250 g/ha, preferably about 4 to 30 g/ha. For field use, where there are losses of herbicide, higher application rates (e.g., four times the rates mentioned above) may be employed.

The active herbicidal compounds of the present invention may also be used in combination with other herbicides. Such herbicides include, for example: N-(phosphonomethyl) glycine ("glyphosate"); aryloxyalkanoic acids such as (2,4-dichlorophenoxy)acetic acid ("2,4-D"), (4-chloro-2-methylphenoxy)acetic acid ("MCPA"), (+/−)-2-(4-chloro-2-methylphenoxy)propanoic acid (MCPP); ureas such as N,N-dimethyl-N'-[4-(1-methylethyl)phenyl]urea ("isoproturon"); imidazolinones such as 2-[4,5-dihydro-4-methyl-4-(1-methylethyl)-5-oxo-1H-imidazol-2-yl]-3-pyridinecarboxylic acid ("imazapyr"), a reaction product comprising (+/−)-2-[4,5-dihydro-4-methyl-4-(1-methylethyl)-5-oxo-1H-imidazol-2-yl]-4-methylbenzoic acid and (+/−)-2-[4,5-dihydro-4-methyl-4-(1-methylethyl)-5-oxo-1H-imidazol-2-yl]-5-methylbenzoic acid ("imazamethabenz"), (+/−)-2-[4,5-dihydro-4-methyl-4-(1-methylethyl)-5-oxo-1H-imidazol-2-yl]-5-ethyl-3-pyridinecarboxylic acid ("imazethapyr"), and (+/−)-2-[4,5-dihydro-4-methyl-4-(1-methylethyl)-5-oxo-1H-imidazol-2-yl]-3-quinolinecarboxylic acid ("imazaquin"); diphenyl ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile ("bromoxynil"); sulfonylureas such as 2-[[[[(4-chloro-6-methoxy-2-pyrimidinyl)amino]carbonyl]amino]sulfonyl]benzoic acid ("chlorimuron"), 2-chloro-N-[[(4-methoxy-6-methyl-1,3,5-triazin-2-yl)amino]carbonyl]benzenesulfonamide ("chlorsulfuron"), 2-[[[[[(4,6-dimethoxy-2-pyrimidinyl)amino]carbonyl]amino]sulfonyl]methyl]benzoic acid ("bensulfuron"), 2-[[[[(4,6-dimethoxy-2-pyridinyl)amino]carbonyl]amino]sulfonyl]-1-methyl-1H-pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N-[[(4-methoxy-6-methyl-1,3,5-triazin-2-yl)amino]carbonyl]benzenesulfonamide ("triasulfuron"); 2-(4-aryloxyphenoxy)alkanoic acids such as (+/-)-2-[4-[(6-chloro-2-benzoxazolyl)oxy]phenoxy]propanoic acid ("fenoxaprop"), (+/-)-2-[4-[[5-(trifluoromethyl)-2-pyridinyl]oxy]phenoxy]propanoic acid ("fluazifop"), (+/-)-2-[4-(6-chloro-2-quinoxalinyl)oxy]phenoxy]propanoic acid ("quizalofop"), and (+/-)-2-[-(2,4-dichlorophenoxy)phenoxy]propanoic acid ("diclofop"); benzothiadiazinones such as 3-(1-methylethyl)-1H-2,1,3-benzothiadiazin-4(3H)-one 2,2-dioxide ("bentazone"); 2-chloroacetanilides such as N-butoxymethyl)-2-chloro-2',6'-diethylacetanilide ("butachlor"); arenecarboxylic acids such as 3,6-dichloro-2-methoxybenzoic acid ("dicamba"); and pyridyloxyacetic acids such as [(4-amino-3,5-dichloro-6-fluoro-2-pyridinyl)oxy]acetic acid ("fluroxypyr").

It is apparent that various modifications may be made in the formulation and application of the compounds of this invention without departing from the inventive concepts herein as defined in the claims.

What is claimed is:
1. A compound of formula:

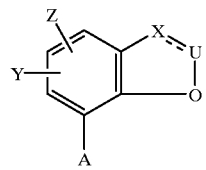

wherein A is:

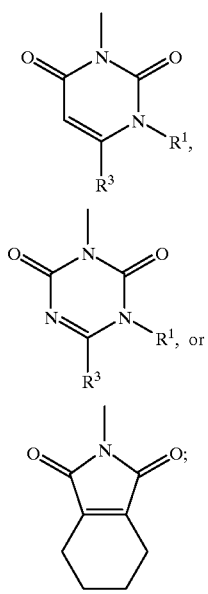

wherein:

U=NR and X is attached to U by a single bond;
R=alkyl, alkenyl, alkoxycarbonylalkyl, (alkoxycarbonyl)haloalkyl, benzyl, phenyl, or cyanoalkyl;
X=CO;
$R^1$=H, alkyl, haloalkyl, or amino;
$R^2$=halogen, alkyl, alkoxy, cyanoalkoxy, phenyl optionally substituted with one or more halogen or alkyl groups, alkoxycarbonyl, alkoxycarbonylalkoxy, benzyl, benzyloxy, or haloalkyl;
$R^3$=alkyl or haloalkyl;
Y=H, halogen, cyano, or haloalkyl; and
Z=H or halogen.

2. A compound of claim 1 wherein R is alkyl; $R^1$ is alkyl, haloalkyl, or amino; $R^2$ is alkyl or phenyl; $R^3$ is $CH_3$ or $CF_3$; and Y and Z are independently H or halogen.

3. A compound of claim 2 wherein A is

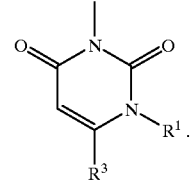

4. A compound of claim 3 wherein R is methyl or isopropyl; $R^1$ is methyl, difluoromethyl, or amino; $R^3$ is methyl or trifluoromethyl; Y is H or 4-halo; and Z is H or 6-halo.

5. A compound of claim 4 wherein $R^1$ is methyl or amino; $R^3$ is trifluoromethyl; Y is H or 4-chloro and Z is H, 6-chloro, or 6-fluoro.

6. A compound of claim 4 wherein $R^1$ is difluoromethyl; $R^3$ is methyl; Y is H or 4-halo; and Z is H or 6-halo.

7. A compound of claim 1 wherein R and $R^1$=$CH_3$; Y and Z=H; and $R^3$=$CF_3$.

8. A compound of claim 1 wherein R and $R^1$=$CH_3$; Y=4-Cl; Z=H; and $R^3$=$CF_3$.

9. A compound of claim 1 wherein R and $R^1$=$CH_3$; Y=H; Z=6-Cl; and $R^3$=$CF_3$.

10. A compound of claim 1 wherein R and $R^1$=$CH_3$; Y=4-Cl; Z=6-Cl; and $R^3$=$CF_3$.

11. A compound of claim 1 wherein R and $R^1$=$CH_3$; Y=4-Br; Z=H; and $R^3$=$CF_3$.

12. A compound of claim 1 wherein R and $R^1$=$CH_3$; Y=H; Z=5-Br; and $R^3$=$CF_3$.

13. A compound of claim 1 wherein R=$CH(CH_3)_2$; $R^1$=$CH_3$; Y and Z=H; and $R^3$=$CF_3$.

14. A compound of claim 1 wherein R=$CH(CH_3)_2$; $R^1$=$CH_3$; Y=4-Cl; Z=H; and $R^3$=$CF_3$.

15. A compound of claim 1 wherein R=$CH(CH_3)_2$; $R^1$=$CH_3$; Y=4-Cl; Z=6-Cl; and $R^3$=$CF_3$.

16. A compound of claim 1 wherein R=$CH(CH_3)_2$; $R^1$=$CH_3$; Y=4-Br; Z=H; and $R^3$=$CF_3$.

17. A compound of claim 1 wherein R=$CH(CH_3)_2$; $R^1$=$NH_2$; Y=4-Br; Z=H; and $R^3$=$CF_3$.

18. A compound of claim 1 wherein R=$CH_3$; $R^1$=$NH_2$; Y=4-Cl; Z=6-F; and $R^3$=$CF_3$.

19. A compound of claim 1 wherein R=$CH_3$; $R^1$=$CH_3$; Y=4-Cl; Z=6-F; and $R^3$=$CF_3$.

20. A compound of claim 1 wherein R=$CH_3$; $R^1$=$CH_3$; Y=4-Cl; Z=6-F; and $R^3$=$CF_3$.

21. A compound of claim 1 wherein R=$CH(CH_3)_2$; $R^1$=$CH_3$; Y=4-Cl; Z=6-F; and $R^3$=$CF_3$.

22. A compound of claim 1 wherein R=$CH_3$; $R^1$=$CHF_2$; Y=4-Cl; Z=F; and $R^3$=$CH_3$.

23. A compound of formula:

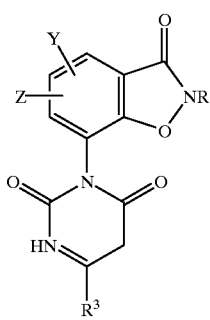

wherein: R=alkyl or alkenyl; R³ is methyl or trifluoromethyl; Y=H, halogen, cyano, or haloalkyl; and Z=H or halogen.

24. A compound of formula:

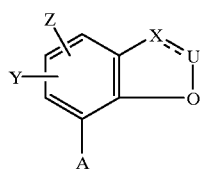

wherein A is:

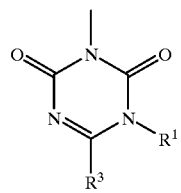

wherein:

U=N and X is attached to U by a double bond;

R=H, alkyl, alkenyl, alkoxycarbonylalkyl, (alkoxycarbonyl)haloalkyl, benzyl, phenyl, or cyanoalkyl;

X=CR²;

R¹=H, alkyl, haloalkyl, or amino;

R²=halogen, alkyl, alkoxy, cyanoalkoxy, phenyl optionally substituted with one or more halogen or alkyl groups, alkoxycarbonyl, alkoxycarbonylalkoxy, benzyl, benzyloxy, or haloalkyl;

R³=alkyl or haloalkyl;

Y=H, halogen, cyano, or haloalkyl; and

Z=H or halogen.

25. A herbicidal composition comprising a herbicidally effective amount of a compound of claim 1 and an agriculturally acceptable carrier therefor.

26. A method of controlling undesired plant growth, comprising application to the locus where the undesired plants are growing or are expected to grow, a herbicidally effective amount of a composition of claim 25.

27. A herbicidal composition comprising a herbicidally effective amount of a compound of claim 1 and a herbicidally effective amount of one or more herbicides selected from the group consisting of glyphosate, 2,4-D, MCPA, MCPP, isoproturon, imazapyr, imazamethabenz, imazethapyr, imazaquin, acifluorfen, bifenox, fomasafen, ioxynil, bromoxynil, chlorimuron, chlorsulfuron, bensulfuron, pyrazosulfuron, thifensulfuron, triasulfuron, fenoxaprop, fluazifop, quizalofop, diclofop, bentazone, butachlor, dicamba, and fluroxypyr.

28. A method of controlling undesired plant growth, comprising application to the locus where the undesired plants are growing or are expected to grow, a herbicidally effective amount of a composition of claim 26.

* * * * *